United States Patent [19]

Kennedy

[11] Patent Number: 5,360,446
[45] Date of Patent: Nov. 1, 1994

[54] INTERACTIVE PROSTHESIS DESIGN SYSTEM FOR IMPLANTABLE PROSTHESIS

[75] Inventor: Patrick W. Kennedy, Columbia City, Ind.

[73] Assignee: Zimmer, Inc., Warsaw, Ind.

[21] Appl. No.: 993,288

[22] Filed: Dec. 18, 1992

[51] Int. Cl.$^5$ .............................................. A61F 2/28
[52] U.S. Cl. ..................................... 623/16; 623/901; 364/474.24
[58] Field of Search ........... 623/18, 23, 20(U.S. only), 623/16, 901, ; 364/413.13, 474.24

[56] References Cited

U.S. PATENT DOCUMENTS

| B1 4,436,684 | 5/1988 | White | 264/138 |
| 4,365,339 | 12/1982 | Pavkovich et al. | 378/15 |
| 4,436,684 | 3/1984 | White | 264/138 |
| 4,719,913 | 1/1988 | Merwin | 128/303 R |
| 4,778,475 | 10/1988 | Ranawat et al. | 623/23 |
| 4,822,365 | 4/1989 | Walker et al. | 623/20 |
| 4,936,862 | 6/1990 | Walker et al. | 623/23 |
| 4,940,412 | 7/1990 | Blumenthal | 434/267 |
| 5,007,936 | 4/1991 | Woolson | 623/23 |
| 5,041,141 | 8/1991 | Ypma et al. | 623/23 |
| 5,150,304 | 9/1992 | Berchen et al. | 623/18 X |

FOREIGN PATENT DOCUMENTS

| 0479257A1 | 4/1992 | European Pat. Off. . | |
| 3340024 | 5/1985 | Germany | 623/18 |
| 9200045 | 1/1992 | WIPO | 623/18 |

OTHER PUBLICATIONS

David G. Mendes, M.D., F.A.C.S., "The Role of Computerized Tomography Scan in Preoperative Evaluation of the Adult Dislocated Hip", Nov./Dec. 1981, pp. 198–202.

Primary Examiner—David H. Willse
Attorney, Agent, or Firm—Todd A. Dawson

[57] ABSTRACT

The present invention involves a system for interactively designing prosthetic implants using two x-ray images, for example two femoral x-rays for designing a hip implant. The x-rays are scanned into a computer which electronically stores and displays the representations of the images. The computer allows the user to select points on the representations which relate to the location of the hip implant, particularly the medullary canal and other related points. The selected points are associated and stored along with the electronically stored representations. Based on the medullary canal definition and other parameters, an implant topology is generated which may be displayed and templated for medical evaluation. The system allows for the points and other parameters to be altered for calculating another implant topology. Also, the system provides for the automated manufacture of the implant and its corresponding rasp broach wherein the stock material of the implant is milled in an orientation which minimizes gouging, processing time, and tool damage.

24 Claims, 10 Drawing Sheets

INTERACTIVE PROSTHESIS DESIGN SYSTEM FOR IMPLANTABLE PROSTHESIS

BACKGROUND OF THE INVENTION

1. Field of the Invention

The present invention relates to a method and apparatus for designing and manufacturing individualized prosthetic implants. More particularly, the field of the invention involves interactively generating customized prosthetic implants to match specific bone shapes.

2. Description of the Related Art

Medical science has developed the ability to implant devices into human bodies to replace fractured or otherwise damaged or degenerated bones. The prothesis, the artificial part which replaces or supplements the body part, used in bone joint replacement is similar to the joint parts it is replacing. Usually, one part of the prothesis is made of metal and the other part is made of plastic because metal and plastic move against each other with little friction. The metals conventionally used are stainless steel, cobalt-chromium-molybdenum alloy, cobalt-chromium-tungsten-nickel, and titanium alloys all of which are well tolerated by the body, are corrosion resistant, and structurally secure. The plastic conventionally used is ultra-high molecular weight polyethylene which is a smooth, sturdy material that resists cracking and wear. The prothesis is conventionally cemented in place with poly methyl-methacrylate to attach to the adjacent bone or bones.

Typically, a prosthesis replaces only the damaged part of the bone, and is attached to the healthy bone by first filing or scraping the healthy bone with a rasp broach before affixing the prosthesis. Thus, both the rasp and the prosthesis should have a contour generally matching the surface of the healthy bone. Further, portions of the damaged bone may be cut off previous to applying the rasp. For example, in replacing the upper portion of the femur, the femur head is first sawed off and a rasp the shape of the inner canal of the femur is applied to the inner surface of the bone before affixing the prosthetic femur stem.

Implants and their corresponding rasps are conventionally manufactured by milling the implant shape out of stock material. The implants and rasps are first profiled and finished by a milling machine which forms the shape of the implant or rasp by milling up and down a piece of stock material to rough out the general shape before finishing the surfaces. For rasps, the finished piece is further processed to form teeth across its outer surface. In such a manner, many implants and rasps may be mass produced.

Each bone in the human body has a particular contour, and many of their the shapes may be generalized and made for any individual. However, variations in human anatomy are not uniform and consequentially many individuals require customized shapes for their implants. This is particularly true for bones which have complex topographies, e.g., bones in the knee or hip joints.

Processes are known for designing and manufacturing customized implants for such individuals. U.S. Pat. Nos. 4,822,365 and 4,936,862 (both to Walker et al. and referred to as the "Walker patents"), the disclosures of which are explicitly incorporated by reference herein, describe a method for designing an implant which utilizes a data base of implant shapes and sizes and provides a generalized implant topology which is a "best fit" for the individual requiring a customized implant. The method disclosed in the Walker patents requires the use of two x-rays of the bone being replaced, for example a femur. The x-rays are used to provide the computer with data specific to the individual, and the computer then calculates an implant topology which is used to manufacture an implant having a topography corresponding to the calculated topology.

In the femur, often the upper portion of the femur proximal to the hip requires replacement. A prosthetic upper femur stem is typically used to interfit with the internal medullary canal of the femur. Consequently, two x-rays are taken of the upper portion of the femur, a front x-ray (providing a sectional view from the medial to the lateral side) and a side x-ray (providing a sectional view from the anterior to the posterior side).

To gather the data needed for the designing process of the Walker patents, the x-rays are placed on a light board and a cursor connected to a computer is used to indicate points on the outer contour of the medullary canal of the femur. Based on the points selected on that outer contour, a computer program compares the contour of the canal, as defined by points taken from the x-rays, with a data base having contours of a random sampling of known canals. Based on the data base comparison, the program generates a three dimensional topology for a suitable replacement femur stem which matches with the contour of the canal. This computer generated topology may then be used to manufacture an implant and its corresponding rasp.

The difficulty of this method relates to the complexities and inaccuracies involved in selecting and changing the data points from the x-ray. On the first x-ray, the axial center of the femur must be vertically aligned, and points on the periphery of the medullary canal must be selected with sufficient particularity to define its contour. This requires drawing a skew line through the axial center of the femur and measuring the diameter of the femur canal, then multiplying the measured diameter by the x-ray magnification factor to enter the true diameter. The two parallel lines that are defined by the straight portion of the canal are draw out until the medullary canal opens out at the upper or proximal end of the femur. The point of divergence of the canal contour from the parallel lines must be indicated, and several subsequent points must then be indicated to define the contour of the femur extending from the straight portion of the canal. Once the first x-ray is suitably processed, a similar procedure is repeated for the second x-ray.

Once all the points from both x-rays have been selected and entered into the computer, the computer checks those points to make sure that the straight portions of the canal on both x-rays are compatible. If an incompatibility error is detected, then the entire process must be repeated. However, if no incompatibility error is detected, prints may be created which represent the topology generated by the computer program. These prints are typically sent to the physician or hospital for approval of the proposed topology. If changes are required in the proposed topology, the canal points of the x-rays must be re-entered using the procedure described above before a new topology can be generated, which allows for the possibility of human error on the second entry that may result in another rejected topology.

Another potential problem with the design of an implant by the aforementioned process involves the shape of the medullary canal. The medullary canal has a generally oval shaped cross-section, which is wider in the medial/lateral (ML) view than in the anterior/posterior (AP) view. Inconsistencies between the straight portions of the medullary canals, as defined from the AP and ML x-rays, often result in femur stem implants which are larger than the medullary canal. Thus, when the rasping device is inserted into the bone before the implant, often substantial portions of the bone are gouged which weakens the bone.

Other methods are known for determining the shape and size of an implant which utilize computerized tomographic methods. Computerized Axial Tomographic (CAT) scanners include cathode ray tube (CRT) devices, nuclear magnetic resonance (NMR) devices, positron emission (PET) devices, and ultrasonic radiant energy techniques may be utilized to generate a three dimensional topology for an implant. However, CAT scanners are more expensive than x-ray machines, are less commonly available, and require that the computer which generates the topology be connected to the CAT scanner. Also, CAT scan results are more difficult to compare with design topologies than x-ray images.

What is needed is an improved apparatus and method for generating implant design topographies using x-ray images.

Also needed are improved methods of manufacturing the implant and its associated devices.

SUMMARY OF THE INVENTION

The present invention is a system for generating implant topographies using x-ray images, a system capable of storing and manipulating computerized representations of the x-ray images to allow for an interactive design process. The apparatus includes a scanner for reading and electronically recording the x-ray images, a computer for manipulating the electronically recorded images, and a display for graphically illustrating the implant topology. The method of the invention includes digitizing and electronically storing two x-ray images, allowing the user to define the implant parameters using the two digitized images, saving the implant parameters in association with the digitized x-ray images, and calculating a proposed topology for the implant. After generating the implant design topology, the topology may be displayed, the implant parameters may be modified, and a new implant design topology may be created.

Using a hip joint implant as an example, the system starts by scanning in an Anterior/Posterior (AP) x-ray and a Medial/Lateral (ML) x-ray of the femur which has an internal medullary canal in which the implant is to be attached. The dimensions of the medullary canal are critical in designing an implant which is suitable for attachment to the femur. The user is provided with a computer monitor which displays the scanned x-ray images, and the computer allows the user to zoom-in on the important portions of the x-ray. The outline of the medullary canal is selected on both the AP and ML views, including the straight portion of the medullary canal, the center of the femoral head, the lesser trochanter, the periformus fossa, and the greater trochanter. Those critical points are stored as x-y coordinates of the scanned images.

When the medullary canal is defined on one view, for example the AP view, the straight portion of the medullary canal is automatically created on the other view, for example the ML view. This creates a generally cylindrical topology for the lower portions of the rasp and implant, thus minimizing the amount of excess bone which may be gouged by the rasp while still providing a relatively secure fit within the medullary canal. Also, automatically generating the straight portions of the medullary canal avoids inconsistencies which may result from having the medullary canal widths defined by different points in the AP and ML views which may cause an undersirable canal geometry requiring the implant designing software to require re-entry of the canal points.

The implant topology developed by the software is printed and forwarded to the physician or hospital. If a change in the topology is desired, the previously stored points defining the medullary canal may be displayed and changed in accordance with the requested changes. The changes may relate to the medullary canal aspect of the implant or to other implant parameters such as with the stem (straight or bowed from the medial/lateral perspective), the anteversion of the neck, the collar, coatings, surface design, flaring or fluting, and the like. Also, the review process may be conducted electronically by comparing computer displayed templates with the electronically stored x-ray images. Further, the system of the present invention also provides cross-sectional views of the implant topology and the medullary canal so that the proposed topology may be further compared or modified at specific points in the medullary canal.

Also, the invention includes a system for manufacturing the implants. A computer controlled machine mills the topography of the implant out of stock material. The calculated implant topology is used to create a series of instructions by which the machine operates. The implant is milled in a series of axial cross-sections, rather than up and down over the contour lines of the implant. By re-orienting the manufacturing process along axial cross-sections, gouging of the implant material, processing time, and tool damage are reduced when compared to conventional milling techniques.

The invention further includes a system for manufacturing the rasps automatically. With non-standardized implants, the corresponding rasps must be manually machined to form teeth on the outer surface. The invention provides an angled cutting mechanism which may be used with an automated milling machine so that the cutting mechanism may be moved in correspondence with the implant topology to properly form the rasp teeth in a sawtooth shape. With a femur implant, the more distal portions of the rasp are preferably formed first and the teeth cut in, before formation of the neck region.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplifications are not to be construed as limiting the scope of the invention in any manner.

DESCRIPTION OF THE PREFERRED EMBODIMENT

The present invention relates to a system for designing and manufacturing prosthetic implants. For purposes of explanation, the following description relates specifically to the design and manufacture of a stem implant for connecting a femur to a hip. However, one skilled in the art will appreciate the principles of the present invention may be applied to the design and manufacture of a variety of prosthetic implants. Therefore, although the preferred embodiment deals specifically with the design and manufacture of a femur stem implant for connection with a hip, the present invention is readily adaptable to the design and manufacture of many other implants as well.

Figure 11:
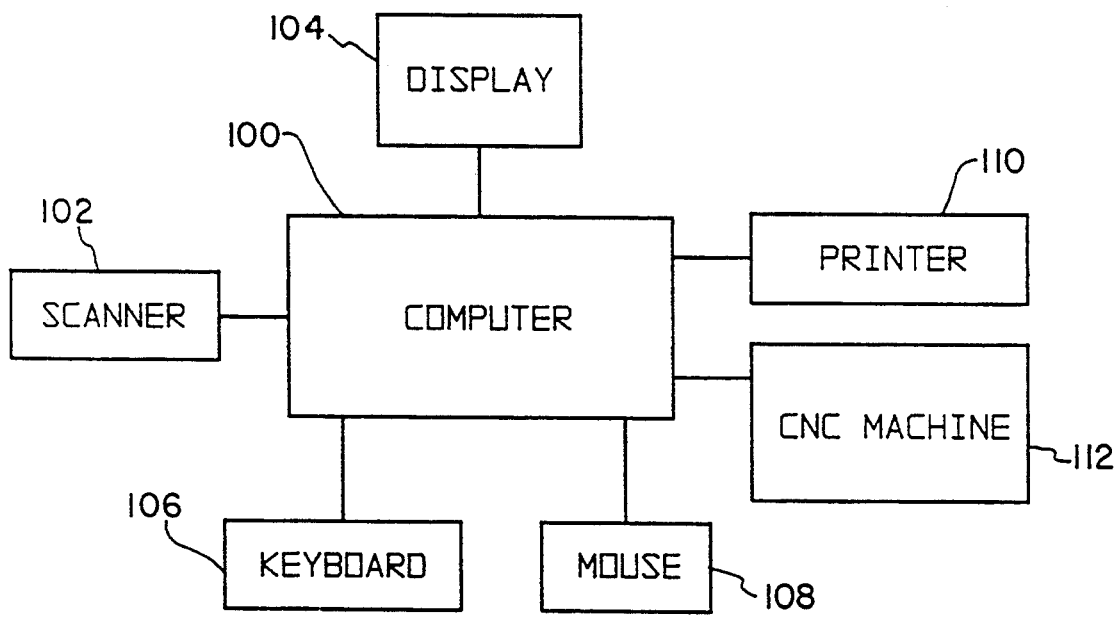
FIG. 11 is a schematic block diagram of the computerized implant design system of the present invention.

FIG. 11 shows a schematic representation of the implant design apparatus which is described in detail below in reference to its operation. Computer 100 is attached to various input/output devices, which allows computer 100 to obtain data regarding a femur, process the data, provide an implant design, and manufacture the implant. Scanner 102 is connected to computer 100 and is adapted to scan in an x-ray image in a conventional manner. Computer 100 is also coupled to video display 104 so that the scanned image may be presented to a user. The user may employ keyboard 106 and mouse 108, which are also connected to computer 100, to select points on the scanned images which define the medullary canal of the femur. Once the points are selected, the computer processes the femur information and generates an implant design topology. The implant design topology may be interactively reconfigured by the user changing the selected points or other design parameters. Based on the implant design topology generated, computer 100 may print out the design on printer 110, or alternatively have the design manufactured by CNC (computer numerical control) machine 112. The various details of the process are described below.

The Femur Stem

Figure 1:
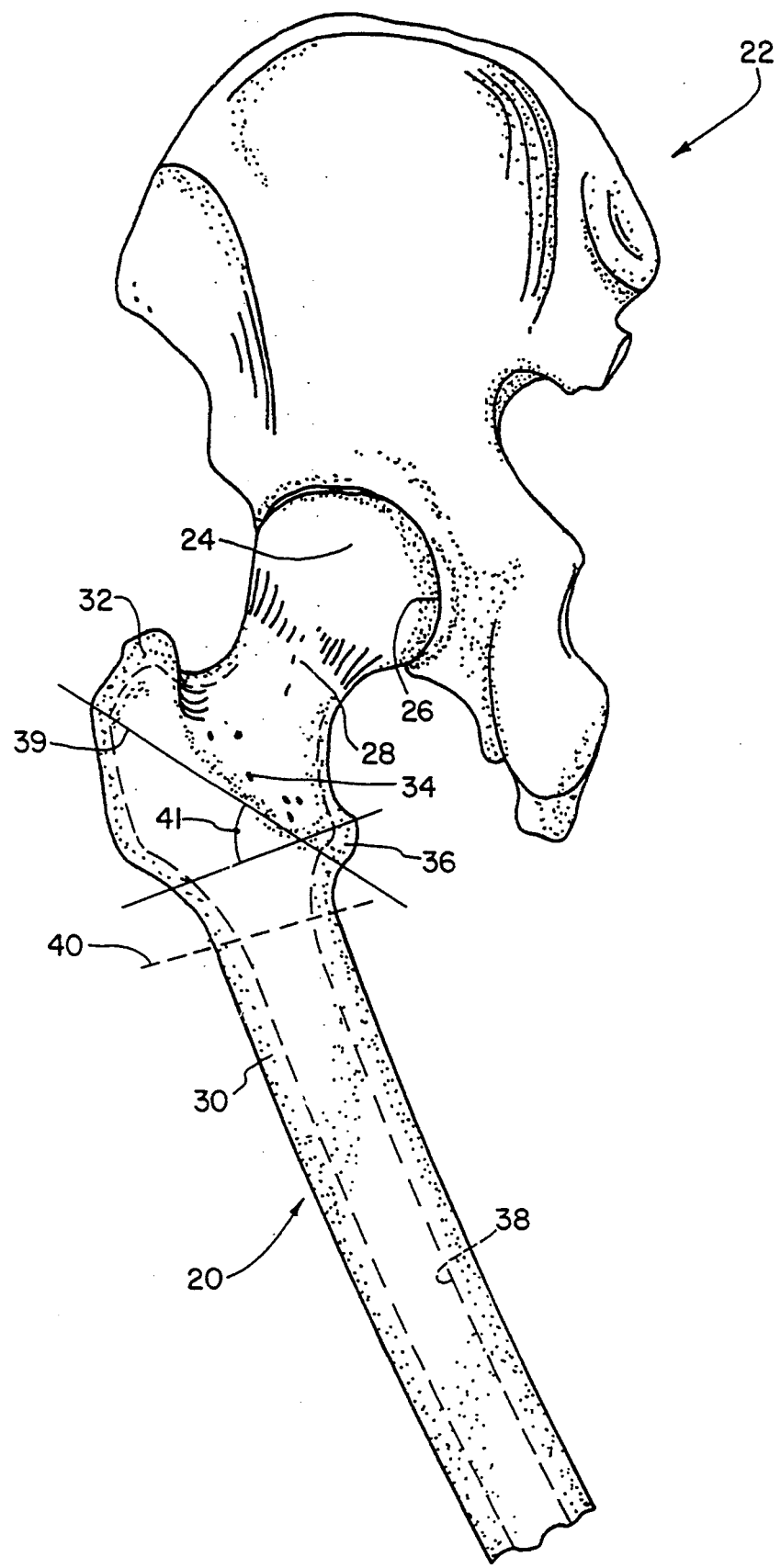
FIG. 1 is perspective view of a femur and ilium of a hip joint.

The femur is a bone in the leg which at its upper end, termed its "stem", forms a joint with the hip. FIG. 1 shows femur 20 and ilium 22 forming a ball and socket type joint at the connection of femoral head 24 with acetabulum 26. Ilium 22 is a part of the innominate or hip bone, which in most mature humans is a fused portion of the hip. Femoral head 24 includes an articular area having the fovea which is in contact with acetabulum 26 of the hip. Femoral neck 28 connects femoral head 24 with medullary canal defining portion 30 of femur 20. Greater trochanter 32, intertrochanter line 34, and lesser trochanter 36 are portions of femur 20 which are located between femoral neck 28 and medullary canal defining portion 30.

Medullary canal 38 is shown in dotted lines and is located within femur 20, and proximal isthmus canal points 40 are indicated at the locations on both sides of the canal where medullary canal 38 transforms from a portion of generally uniform width having parallel sides to an expanding portion having diverging sides. Femoral neck 28 is a frequently fractured bone, and the present invention involves the design of a femoral neck replacement which engages medullary canal 38 and provides a mounting location for a prosthetic femoral head. In the surgical operation in which the fractured femur bone is replaced by an implant, the femur bone is usually sawed at cutting line 39 which is disposed at predetermined osteotomy angle 41 relative to a line perpendicular to the axis of medullary canal 38. Osteotomy angle 41 is determined by the decision of the treating physician and implant engineer, although generally the line defining the osteotomy angle is determined by two points, one of which is about one centimeter above lesser trochanter 36 and the other of which is at the tip of greater trochanter 32.

The X-Rays

Figure 2:
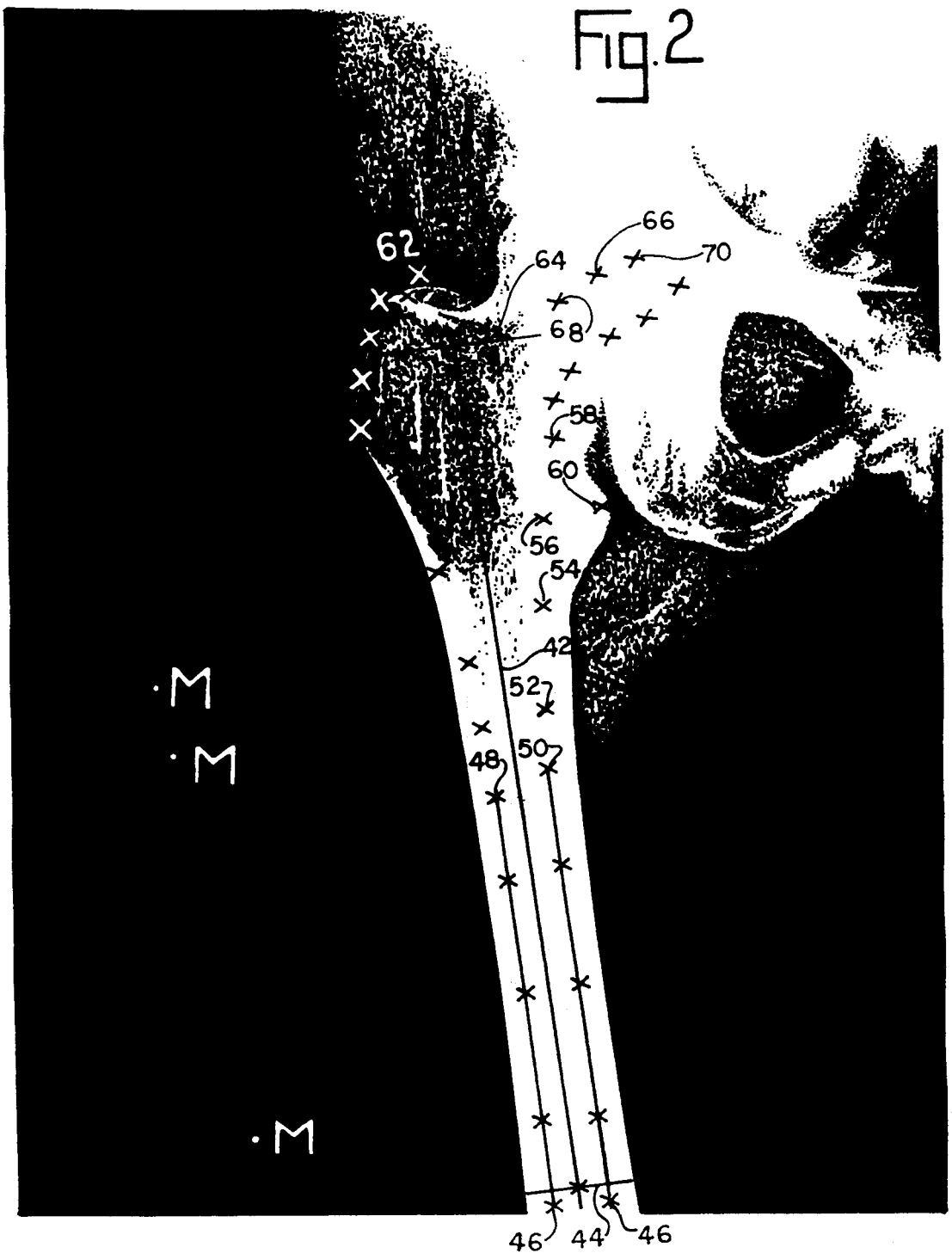
FIG. 2 is an x-ray of an Anterior/Posterior view of a femur and ilium.
Figure 3:
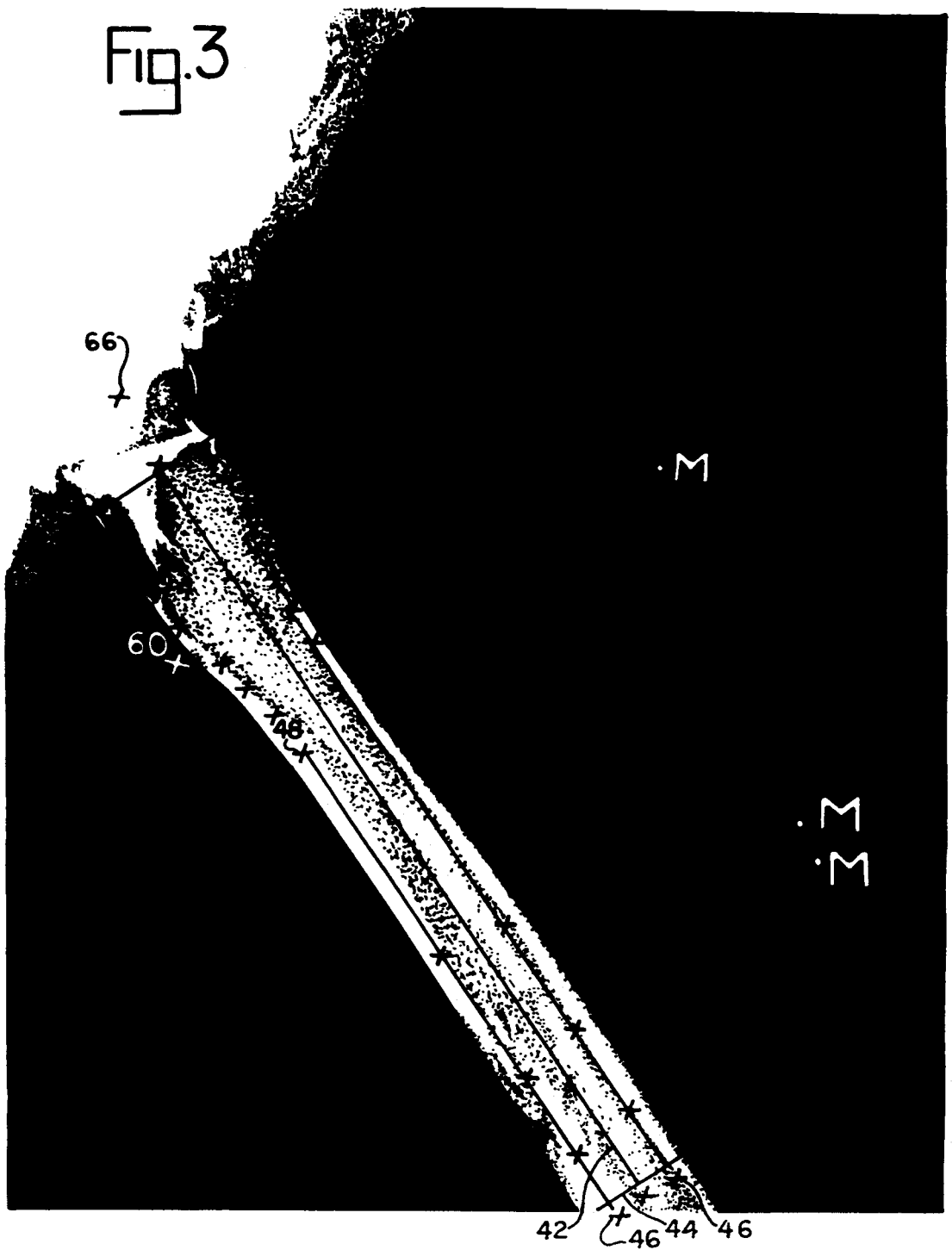
FIG. 3 is an x-ray of a Medial/Lateral view of a femur and ilium.

The first step taken in designing an implant for replacement of the hip joint is to have x-rays taken of the patient's femur and hip, as shown in FIGS. 2 and 3. The x-rays are conventionally taken from the Anterior/Posterior (AP) view of FIG. 2 and from the Medial/Lateral view of FIG. 3. These views are indicative of the size and shape that the implant must have to properly interact with the medullary canal of the femur and replace the femoral head and the acetabulum of the hip joint. In order to calculate the actual size of the prosthetic implant to be designed, both the magnification of the x-ray and the image scanner are calculated by the selection of magnification points (see points labeled M on the x-rays of FIGS. 2 and 3) on the scanned image that the system software processes to derive the actual magnification factors.

For example, two points are used to define first and second scaling points which are a predetermined distance from each other, e.g., 100 mm at the time the x-ray is taken. Then, a third point is made in the x-ray itself so that it is always a predetermined distance from the first scaling point prior to computer scanning. The scanner magnification is calculated as the difference between pixel coordinate values per unit of real measure, e.g., the pixel coordinate (975, 25) is 400 pixels from (575, 25) which are known to be 100 mm apart and therefore the scanner magnification is their ratio, or 4 pixels per mm. The x-ray magnification is calculated as the ratio of the pixel distances between the first and second and the first and third scaling points. Thus, the actual distances on the x-ray may be calculated using the scanner magnification factor (the actual x-ray scale is used to print out the template prints), and the actual dimensions of the bone which was the subject of the x-ray may be calculated using the x-ray magnification factor.

The medullary canal is generally oval shaped in cross-section at its lower portion, and thus may be defined by the location of its axial center, which on the x-rays is shown as skew line 42, and the diameter of the canal, which on the x-rays are shown as diameter 44. Skew line 42 and diameter 44 define medullary canal lines 46 which are parallel to and equidistant from skew line 42. The upper portion of the medullary canal diverges from the straight lines at the most proximal isthmus canal points 48 and 50, and is further defined by points at upper canal 52, 54, 56, and 58 as well as similarly disposed points on the other side of the canal (not numbered).

In order to define the upper portion of the prosthetic, the most proximal canal region is defined by points at lesser trochanter 60, greater trochanter 62, periformus fossa 64, and femoral head center 66. Femoral head center 66 is involved in defining both the neck length and position, lesser trochanter 60 is involved in defining the medial canal position and the osteotomy cut position, periformus fossa 64 is involved in defining how high or proximal the implant extends, and the greater trochanter is involved in defining the osteotomy guide angle. The neck region of the implant is determined by three selected points and by the specification of design parameters. The specified points include femoral head center 66, auxiliary short neck point 68, and auxiliary long neck point 70.

The Design Process

Figure 8:
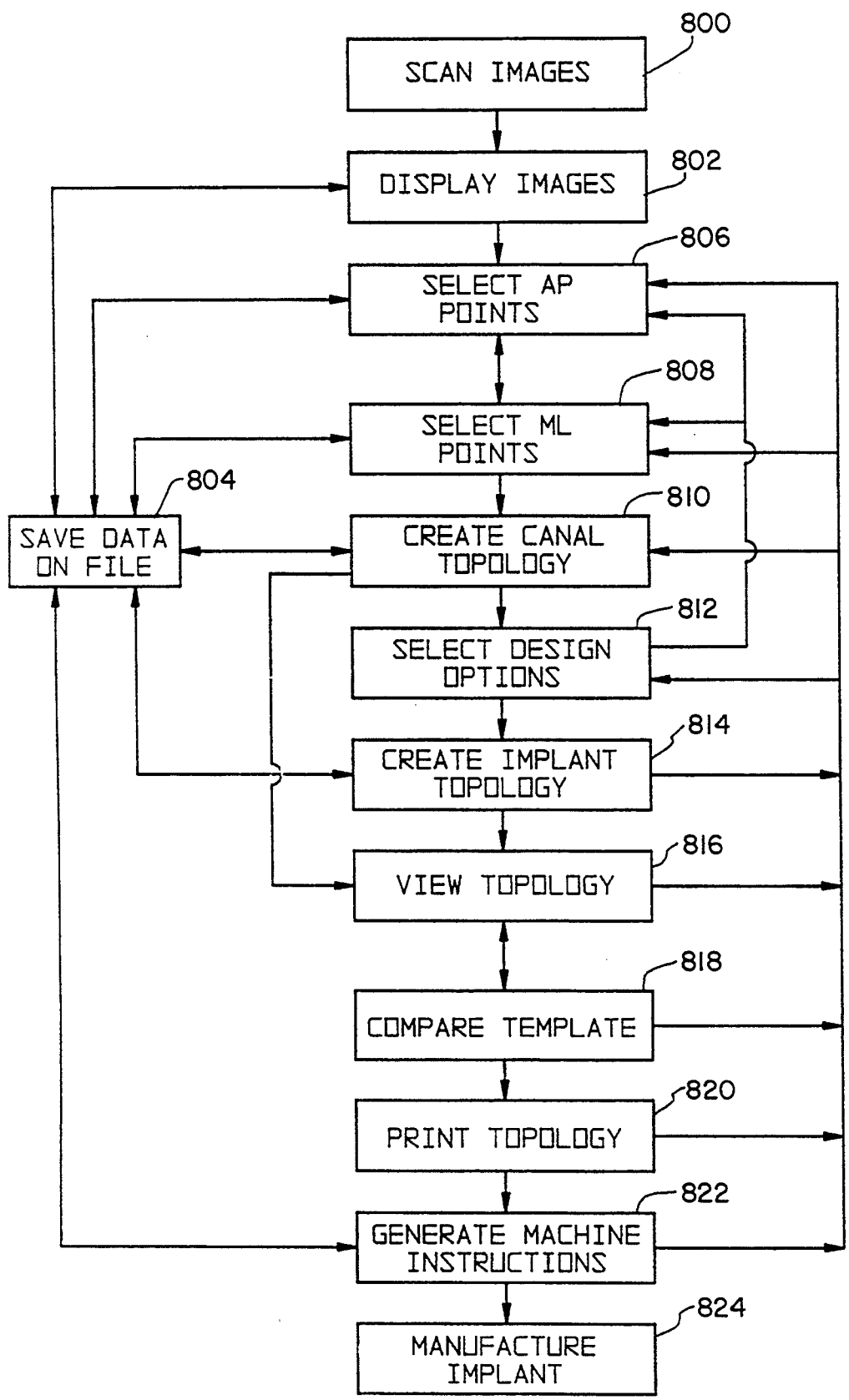
FIG. 8 is a flow chart diagram of the femur stem design system of the present invention.

The overall process of designing and manufacturing a femur stem implant is represented by the flow chart of FIG. 8. The first step, labeled 800, in the process involves scanning the patient's x-rays using a computer and optical scanning equipment as is well known in the art. The scanned representation of each x-ray image (an AP and ML view) provides a data array of pixels, preferably with 256 gray scale pixel values. Each scanned representation is then scaled according to the magnification of the scanner, then displayed in display image step 802. Also, the scanned representation may be saved and stored in a data file in step 804.

The operator may now select the various points on the AP scanned representation in step 806 and on the ML scanned representation in step 808 to define the medullary canal, as will be described in greater detail below. Once all the points are selected, then the medullary canal topology is created by the computer in step 810. After any of steps 806, 808, or 810, the points selected and the topology created may be saved on a file in step 804. Next, design options may be selected in step 812, options which include implant parameters such as those involved with the orientation of the stem (straight or bowed), the anteversion of the neck, the presence and design of the collar, any coatings for the implant, specific surface designs, and any flaring or fluting, and the like. Further, after selecting the design options, the operator may alter selected points in steps 806 and 808, if desired.

Assuming all points and options have been suitably selected, the implant topology is created in step 814, as will be described in greater detail below. After the creation of the topology, it may be saved on a file in step 804 and further may be displayed in step 816. Note that the canal topology created in step 810 may also be displayed in step 816, providing however that the process returns to step 810 so that an implant topology may be created. Step 818 allows for the simultaneous display of a scanned representation of an x-ray with a corresponding view of the created topology of implant in compare template step 818, as will be described in greater detail below. The created implant topology may also be printed out in step 820 and forwarded for approval. Next, machine code may be generated in step 822 which instructs a suitably configured automated manufacturing device to produce an implant having the dimensions of the created implant topology, and the machine code may be stored in step 804 for subsequent processing such as step 824 which manufactures the implant.

At any of the steps 814, 816, 818, 820, or 822, the operator may return to the implant specification steps of the process, namely any of steps 806, 808, 810, or 812, to modify the implant design. Further, the implant specifications may be altered from the saved file, using the same data as the original design. A significant advantage of the present invention is that the previously entered information in the implant specification steps does not require re-entry to change the implant design. Typically, the medical personnel who review the implant topology are removed from the implant design process, and such re-entry may introduce errors in the design. Also, the physician or engineer may interactively change implant design parameters, including changing the location of selected points on the scanned x-ray images, and compare the resulting implant design topology with the scanned x-ray images on the display.

The Entry of Femur Canal Data

Figure 9:
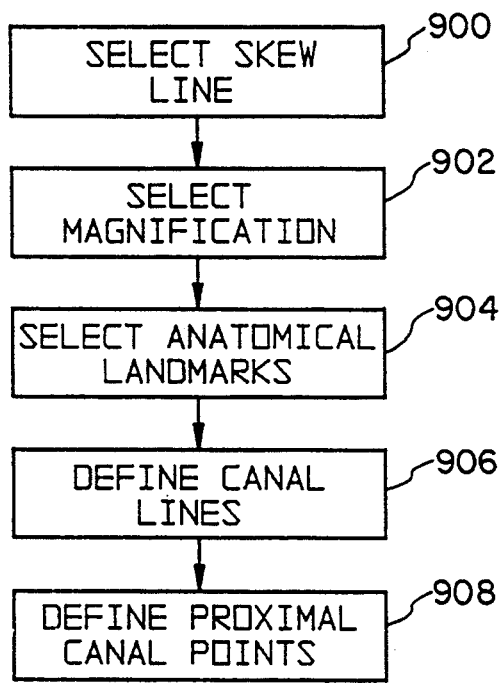
FIG. 9 is a flow chart diagram of the general x-ray point selection process.

A general overview of the point selection process for each x-ray is shown in FIG. 9. The first step is Select Skew Line 900 in which the user first indicates the bottom point of the skew line of the medullary canal, then the user indicates a second point to define the axially centrally located skew line. The second step is Select Magnification 902 in which the user indicates the three magnification points on the x-ray which determine the scaling of the x-ray image. After the image has been scaled, Select Anatomical Landmarks 904 is the next step which allows the user to indicate some significant points to the implant design. On the AP x-ray, the femoral head center, the lesser trochanter, the periformus fossa, and the greater trochanter are identified, while on the ML x-ray only the femoral head and the lesser trochanter need be identified. After defining the skew line and the femoral head, the canal lines are indicated in Define Canal Lines 906 by selecting two points which define the skew line of the canal. In the AP view, the initial generation of the straight portions is accomplished by specifying a width around the skew line; while in the ML view the straight portions are automatically generated after the skew line points are selected. Then in Define Proximal Canal Points 908, the user selects a most proximal isthmus canal point and at least five subsequent points on each side, with the computer software automatically selecting five points along the straight portion of the canal. The user defines the medullary canal by selecting points on the Lateral/Medial and the Anterior/Posterior canal walls of the scanned x-rays.

Figure 10:
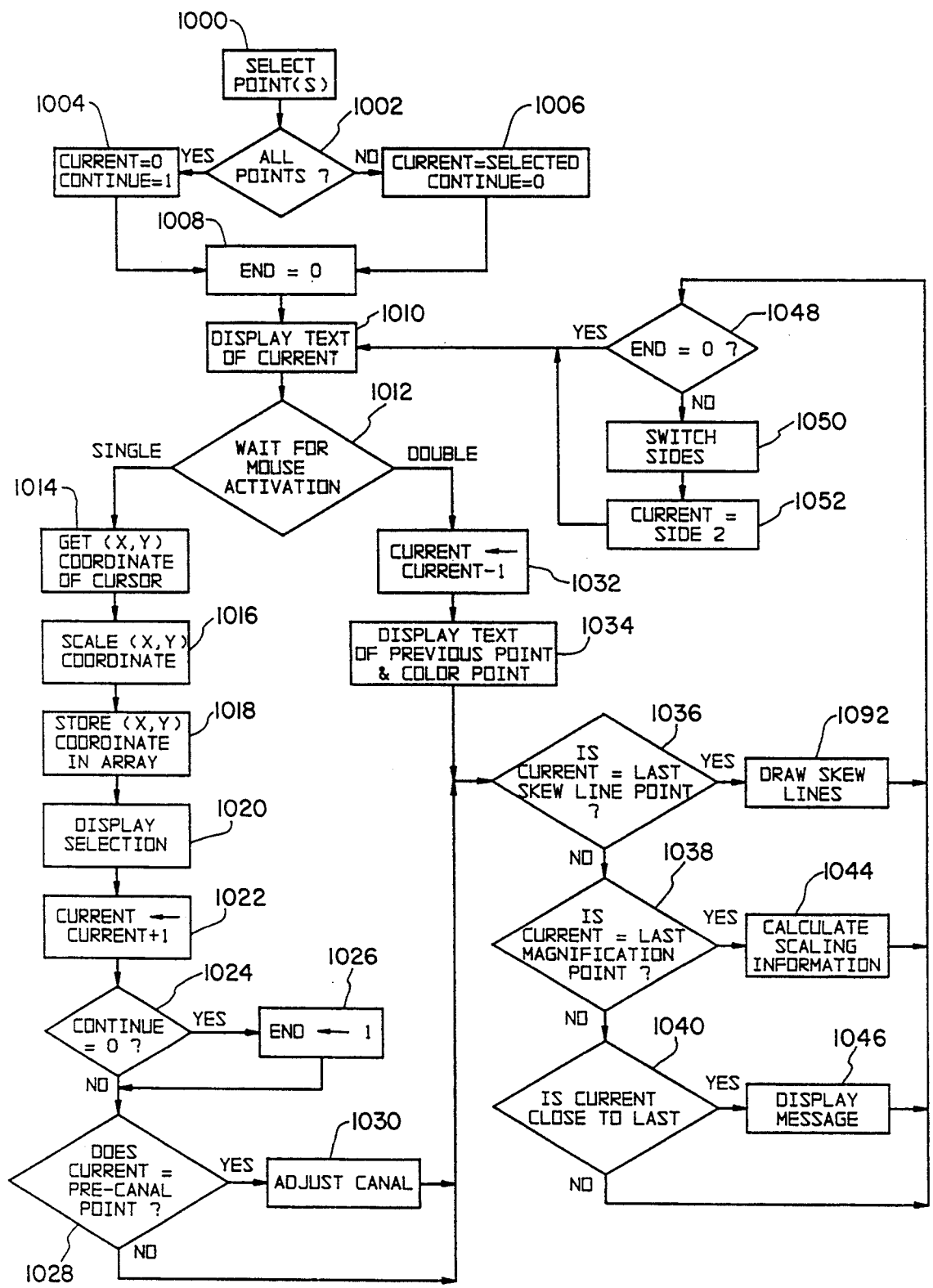
FIG. 10 is a flow chart diagram of the computer x-ray point entry algorithm.

The algorithm executed by the computer software to perform the general steps of FIG. 9 is described in greater detail in the following discussion of FIG. 10. The process is implemented using a computer with a graphic user interface having a mouse, i.e., a device which moves a cursor around a graphic display such as a video monitor. In the present invention, the mouse utilized is capable of two differentiable types of activation, e.g., a single or a double pressing of a button. However, differentiable types of activation may be accomplished by having two buttons, or by timing the length of the button depression. Furthermore, other interfacing techniques may be used in accordance with the present invention, such as using special keyboard character sequences, a mouse with two buttons, a light pen, a joy stick, or a variety of other ways known to one of ordinary skill in the computer programming art. Also, image processing techniques such as enlargement and scaling may be employed.

Select Points 1000 represents the first step of the point selection process, in which the user indicates whether the displayed image is being edited or whether a new scanned image is being defined. In step 1002 the computer decides whether all points are to be defined or whether the currently selected point is being changed. If all points are to be defined, then step 1004 sets the variable CURRENT to 0 and the variable CONTINUE to 1, otherwise step 1006 sets CURRENT to the number associated with the currently selected point, ceases to display the previous position of the selected point, and sets CONTINUE to zero. The variable CURRENT represents the index into the storage array for that x-ray, with many of the array locations being associated with a specific point of the femur. The variable CONTINUE indicates whether the user is entering values for the first time, or whether only one point is being modified. In either case, the variable END is then set to 0 at step 1008 and the main loop of the algorithm starts at step 1010.

The user is prompted with a box containing text describing the nature of the next point which that user must select in step 1010. In step 1012 the computer waits for a single or double activation of the mouse switch. The mouse may be activated regardless of whether the cursor is located within the x-ray image. If the cursor is outside the x-ray image, the mouse activation may be used to initiate another function such as a pull-down menu. In the case of a single activation of the mouse when the cursor is within the x-ray image, the (x,y) coordinates of the cursor on the display are determined in step 1014, those coordinates are scaled in step 1016 (if scaling information has been obtained), and are stored in an array of selected points in step 1018. The selected point is graphically displayed in step 1020, for example by a circle or an "x". The variable CURRENT is incremented by one in step 1022 and then the variable CONTINUE is checked in step 1024. If CONTINUE is equal to 0, then the variable END is set to 1 in step 1026, and the variable CURRENT is checked in step 1028 to see if the medullary canal lines are to be defined.

If CURRENT indicates the point which is defined previous to the definition of the medullary canal, then the straight lines of the medullary canal are created in Adjust Canal step 1030. For the AP x-ray, the greater trochanter is the point previous to Adjust Canal step 1030 which involves using a scroll box or similar technique to designate the width of the canal. For the ML x-ray, the last entered magnification point is the point previous to Adjust Canal step 1030 involves automatically creating a pair of straight, parallel lines centered around the skew line with one side of the canal lines being highlighted for further selection of points on that side of the canal. After Adjust Canal step 1030, special points are checked for as discussed below relating to steps 1036, 1038, and 1040.

Referring back to step 1012, the mouse being subject to a double activation allows the user to indicate that the previously entered point is to be adjusted. In this case, the CURRENT variable is decremented in step 1032. Also, in step 1034, the text associated with that point is displayed and the point is activated by highlighting or is displayed in another color on the display. After reactivating the previous point in response to the double activation of the mouse, three special cases are checked for in steps 1036, 1038, and 1040.

The special case of the selection of the second point of the skew line is checked for in step 1036. If the newly selected point is the second skew line point, then the skew line is created and displayed in step 1042. The special case of the selection of the last magnification point is checked for in step 1038. If the newly selected point is the last magnification point, then scaling information used in step 1016 is calculated and the stored values of any previously entered points are scaled and adjusted in step 1044. The special case of the storage array running out of room is checked for in step 1040. If the newly selected point is close to filling the array, then a warning message is displayed in step 1046. Further, if the array is full for that side of the canal points, the variable END is set to 1 in step 1046.

After checking for the above described special cases, the comparison portion of the loop includes step 1048 which tests the value of the variable END. If the variable END equals zero, then the loop is repeated by starting again at step 1010. Otherwise, however, the computer determines whether the other side of the canal requires points to be selected in Switch Sides step 1050. If the other side of the canal is undefined, then CURRENT is set to the first index value for the second side (represented on the flow chart as "Side2") in step 1052 and the loop is repeated by starting again at step 1010. If both sides of the canal have been defined, then the loop is completed.

If particular points need to be redefined, the user should select the point to be modified and the algorithm may be started at step 1000. In step 1002, the user would indicate that only the selected point is to be modified. Once in the loop portion of the algorithm, any of the previously selected points may be modified as described above. The algorithm is applicable to either the AP or ML views of the x-ray. Thus, the algorithm of FIG. 10 may be used for initial entry and for subsequent modification of either view.

However, the specific points and sequence in which they are entered differ between the AP and ML views. In the AP view, the user first selects the bottom skew line point, then the top skew line point. Next, the user selects the three magnification points. The points that the user subsequently selects are the center of the femoral head, the lesser trochanter, the periformus fossa, and the greater trochanter. At this point, the user is presented with a scroll box which controls the width between the straight, parallel lines on each side of the skew line. The display includes an indication of the skew line as a large "I" with the bottom leg of the "I" located at the bottom skew line point and the top leg of the "I" located at the periformus fossa. While the user selects the appropriate width, the computer highlights the straight, parallel lines and prompts the user to select the most proximal isthmus canal point on the first side of the canal. After the entry of the most proximal isthmus canal point, the computer automatically selects five points below the most proximal isthmus canal point to define the lower portion of the canal. Further, the user is prompted to enter at least five points above the most proximal isthmus canal point to define the upper portion of the canal. The user may switch sides after the five points are entered, or the sides may be automatically switched if all the storage array reserved for the first side is taken.

The user first selects the bottom skew line point, then the top skew line point in the ML view as well. Next, the user selects the three magnification points. At this point, the computer automatically creates the straight, parallel lines of the canal. The user subsequently selects the center of the femoral head and the lesser trochanter, as the periformus fossa and the greater trochanter are not well apparent in the ML view. The computer next highlights the straight, parallel lines of the canal and prompts the user to select the most proximal isthmus canal point on the first side of the canal. After the entry of the most proximal isthmus canal point, the computer automatically selects five points below the most proximal isthmus canal point to define the lower portion of the canal. Further, the user is prompted to enter at least five points above the most proximal isthmus point to define the upper portion of the canal. The user may switch sides after the five points are entered, or the sides may be automatically switched if all the storage array reserved for the first side is taken.

After the user has selected all the points on both the AP and ML x-rays, the process of the aforementioned Walker Patents may be applied to the digitized points (which are corrected for the skew angle and magnification factors) and a three dimensional model of the medullary canal may be created. The medullary canal distal, or lower, portion has a cylindrical shape defined by the straight, parallel lines and the most proximal isthmus canal points. The medullary canal proximal, or upper, portion is contoured to fit within the digitized upper canal points. If the user wishes to change the shape of the medullary canal, some of the selected points may be modified as disclosed above, and a new canal model created.

The three dimensional model of the medullary canal is stored electronically as twenty-five cross sections which have forty points in each cross section. The twenty-five cross sections each having x,y,z coordinate triplets represent the canal geometry. Thus, three 25 by 40 arrays may be used to store the respective x, y, and z values for each perimeter defining point. This data structure arrangement is dictated by the Walker process, which is well suited for the definition of femur stem implant topographies. This data structure is not directly compatible with the operation of CNC machines, but the data structure may be processed to provide suitable CNC instructions in a manner readily recognizable by one skilled in the art of programming. However, any suitable data structure may be used as long as it is compatible with the design algorithm employed. Thus if a different algorithm was used, or a different part of the body was being modeled, another suitable data structure may be used.

Also, the user enters other implant design parameters in a conventional manner, e.g., by a menu of choices which may be selected and modified. The design parameters include the type of stem (straight or bowed, with the length and any bow radius), any neck anteversion and proximal body twisting (including the degree of anteversion), any collar (with thickness and radius), the neck and osteotomy angle, the distance below the periformus fossa that the implant reaches, whether the implant is for the left or right side, any coating (hydroxyappetite/tri-calcium phosphate), surface type (smooth, macro-fit grooves, or with pockets for porous surfaces), any lateral flare, type of proximal fit (regular, enhanced, or super), and any flutes.

The points entered on the x-rays are stored in computer data structures which include the scanned images of the x-rays, the digitized (x, y) coordinates, and the scaled and digitized (x, y) coordinates. The scanned images may be stored conventionally in a flat file. The coordinates, scaled and unscaled, may be stored as a complex array, e.g., 100 (x, y) pairs stored in an array or a 100 by 1 by 1 array. Further, other information derived from the selected and scaled points is stored which includes the side (left or right), the x and y coordinate offsets, the skew line angles, the neck and osteotomy angles, the stem length, the distance below the periformus fossa, and the locations of the distal tapper, the medial fit, greater and lesser trochanter, and the femoral head. In addition, patient, physician, hospital, and other related information may be stored as text or numerical fields in an associated data file.

The Design of an Implant

Previous to the design of a particular implant, a computer model of an average bone is developed in accordance with the teachings of the aforementioned Walker patents. Once the model of the average bone is developed, the x-rays of the patient are scanned and the data points on the x-rays are specified as described above. The actual data points selected from the patient x-ray are compared to the model of an average femur, and the implant topology is adjusted to conform with the difference. Further, the data points may be modified subsequently to the initial generation of the implant topology, then the design process of the Walker patents may be again employed.

In accordance with the process described in the Walker patents, the present invention includes the ability to specify and subsequently modify design parameters. One such design parameter is whether the stem is to be bowed, that is curved in its medial/lateral view, and if bowed then the center and radius of the curvature are specified. In regards to the neck portion of the implant, the neck angle, anteversion and the anteversion angle, and the collar thickness and radius may be specified. In the mid sections of the implant, the distance below the periformus fossa which the non-cylindrical portion of the stem extends, the osteotomy angle at which the femur is sawed, any porous surface pockets, and any grooves may be specified. Also, any fluting and the medial fit (either normal, premium, or super) are design parameters which may be specified.

The Testing and Approval of the Implant Design

The implant topology is a mathematical model of the size and shape of the implant which has been created according to the above mentioned process of implant design. The resulting femoral stem implant may be like stem 72 shown in FIG. 4A with similarly shaped femoral rasp broach 74 shown in FIG. 4B, or of any other known type of femur stem implant. Also, osteotomy guide 128 of FIG. 4C is conventionally manufactured in accordance with the implant topology and the designated osteotomy angle.

Figure 4:
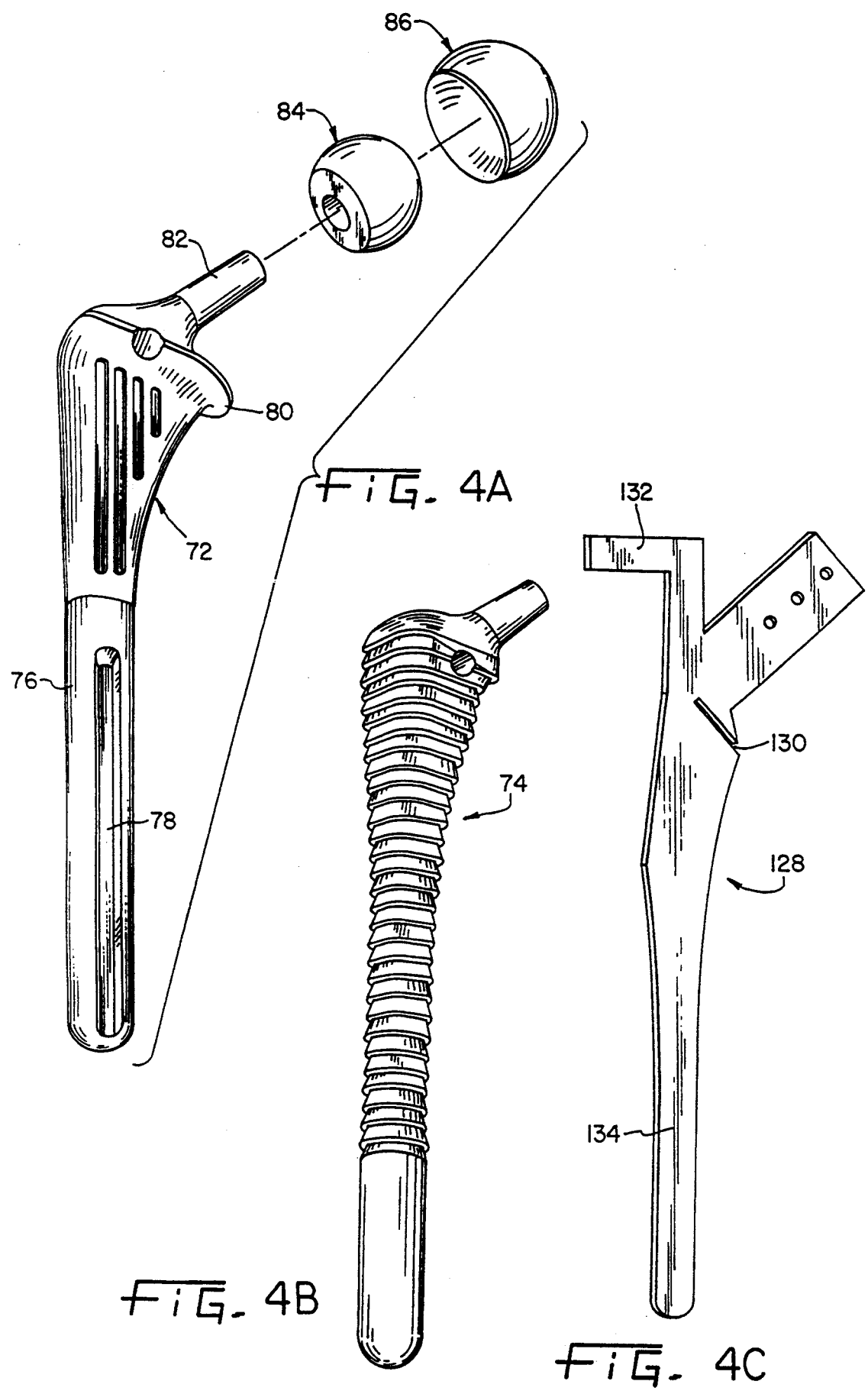
FIG. 4A is a perspective view of a femur stem implant with associated femoral head, acetabular shell, and liner.
FIG. 4B is a perspective view of a rasping broach corresponding to the shape of the femur stem of FIG. 4A.
FIG. 4C is a perspective view of an osteotomy guide corresponding to the shape of the femur stem of FIG. 4A.

Referring to FIG. 4A, base portion 76 may have ridge 78 for aiding in stem 72 setting in the actual medullary canal of the patient's femur. The upper portion of stem 72 may include collar 80 from which extends neck portion 82. Neck portion 82 is generally cylindrically shaped to be connected to femoral head replacement 84. Head 84 has an aperture which receives neck portion 80, and has an articulated outer surface which forms a ball and socket type joint with acetabular shell and liner 86. Also, the middle and upper portions of rasp broach 74 of FIG. 4B are formed with a sawtooth like surface for rasping the femur, which is described in greater detail below.

Referring to FIG. 4C, osteotomy guide 128 includes saw guide slot 130, greater trochanter arm 132, and femur stem 134. By locating greater trochanter arm 132 on the tip of the greater trochanter and aligning femur stem 134 with the actual femur bone, a bone cutting saw may be located in saw guide slot 130 so that an initial cut may be made into the femur bone. Osteotomy guide 128 is then removed and the top of the femur is sawed off.

Figure 5:
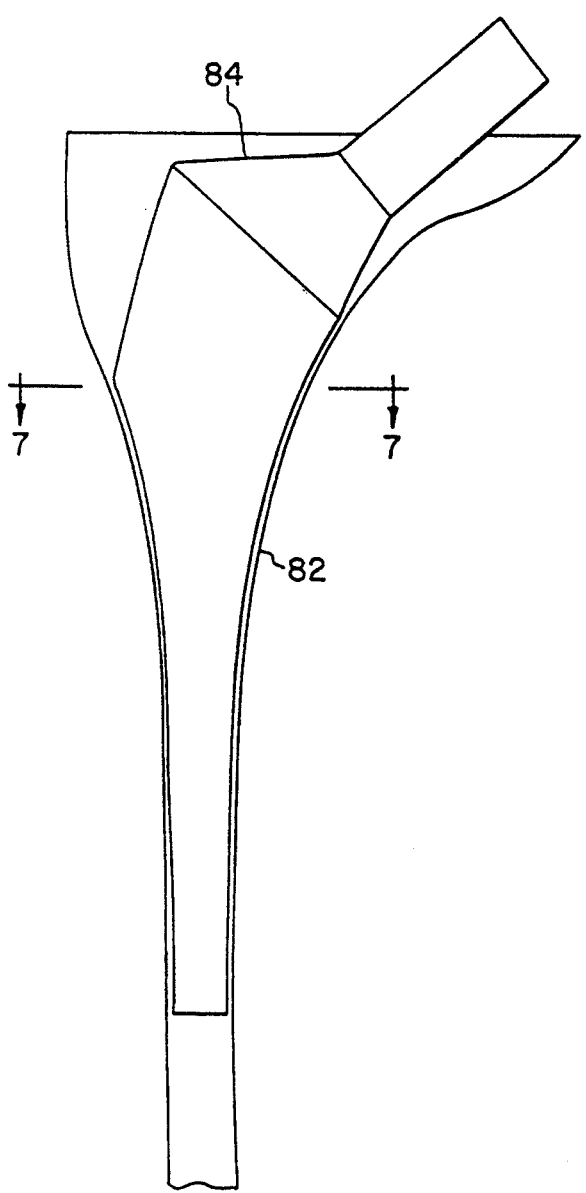
FIG. 5 is an Anterior/Posterior view of a computer generated topology for a femur stem implant.
Figure 6:
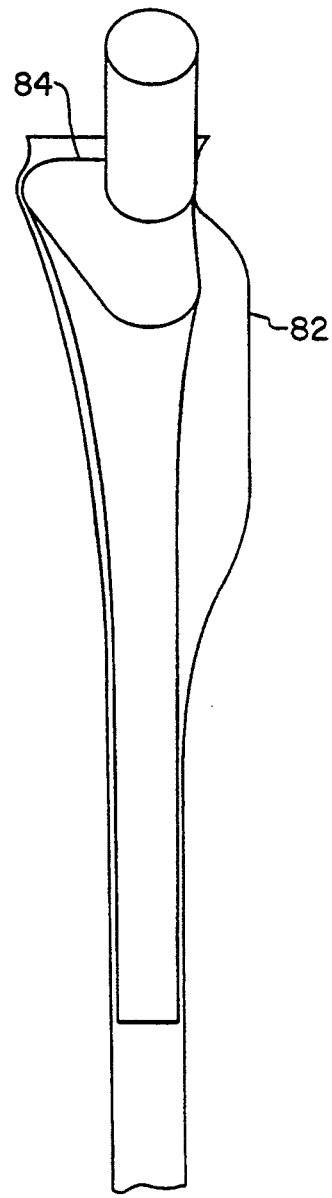
FIG. 6 is a Medial/Lateral view of a computer generated topology for a femur stem implant.
Figure 7:
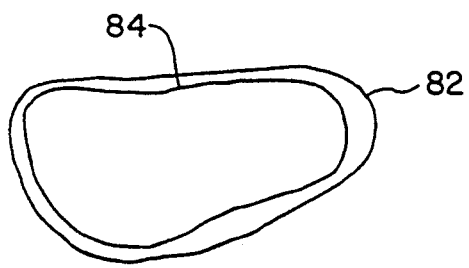
FIG. 7 is a cross-sectional view of a computer generated topology for a femur stem implant taken along view lines 7—7 of FIG. 5.

The actual outer contours of stem 72 and rasp broach 74, and the general outline of osteotomy guide 128, are defined by the computer model depicted in FIGS. 5–7. FIGS. 5 and 6 show front and side views, respectively, of medullary canal model 82 and corresponding implant topology 84. FIG. 7 shows a cross-sectional view of medullary canal model 82 and implant topology 84. Such a cross-sectional view may be generated at any point of the topology. These representations may be generated by a computer and viewed on the graphic display.

Further, implant topology 84 may be superimposed on scanned x-ray images by use of a menu option. The template option displays both the scan of the x-ray and the outline of the implant, with the user having the option of moving and/or rotating the implant outline. The template actually appears translucent because the pixels associated with the lines of the outline have their gray scale value reversed by an exclusive OR ("XOR") operation on its own value. The translucent outline is easily moved on the display by XORing both the old and new locations of the outline. Thus, the physician or other medical personnel may use the graphic display of the computer system to evaluate the implant design topology.

Further, the computer generated models may be printed out to allow prints of the design topology to be shipped away for evaluation. For example, manufacturing prints, templates, surgeon approval prints, and case information prints may be generated. The manufacturing print references the extraction hole location of the material to be machined into the implant, and contains the following information:
  distal stem diameter
  3 cross-sectional diagrams and measurements
  total stem length
  anteversion angle
  bow radius
  flute depth and location
  macro-fit groove depth and location
  pocket geometry
  neck angle
  neck offset
  extraction hole location
  collar radius and thickness
  collar location
  etch location
  neck taper dimensions Preferably, the manufacturing print is prepared using a plotting machine using C sized drafting paper.

The template prints include AP and ML outline views of the implant which are scaled to the actual x-rays so that the physician may physically superimpose the implant design on the x-ray. In addition to the implant outline, the physician approval print includes the following information:
  distal stem diameter
  3 cross-sectional diagrams and measurements
  total stem length
  anteversion angle
  bow radius
  neck angle
  neck offset These prints, and most other prints, are preferably prepared on letter sized paper using a Hewlett Packard/Graphics Language compatible printer.

Also, an associated data file is employed to record information regarding the patient. This information is keyed in a conventional manner, and may include information identifying the patient, physician, engineer, and case number. Other associated information may include whether the design is for a revision or primary implant; whether it is for a left or right femur; the design and surgery date; the prognosis; the item and etch numbers; the patient's weight, height, and age; the current state of activity; the fit type; the coating type; flute type; collar type; surface type; and stem information such as its length and whether it is bowed.

The Manufacture of an Implant

Figure 12:
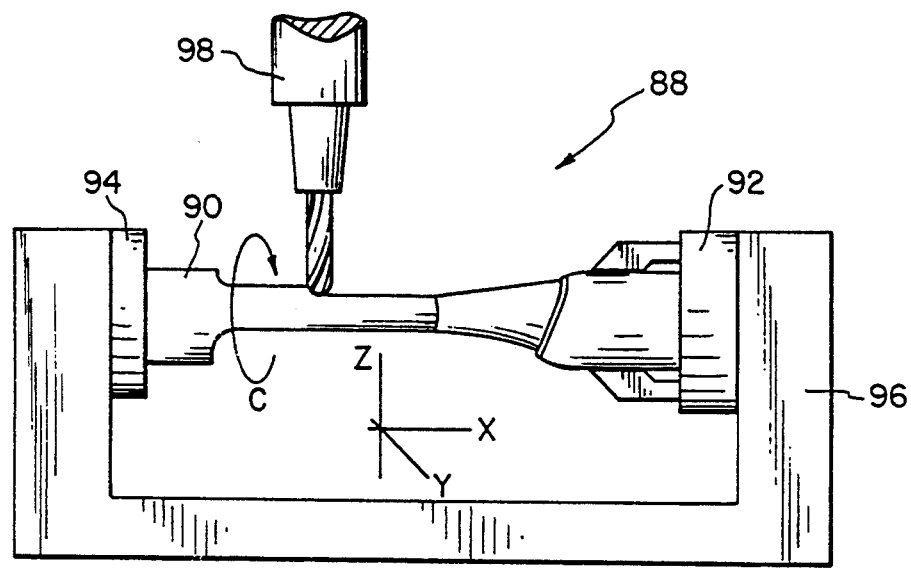
FIG. 12 is a perspective view of a four axis machine milling a piece of stock material for forming a femur stem.

The apparatus which manufactures the femur stem implant is shown in FIG. 12. CNC machine 88 is termed a four axis machine for its ability to move stock material 90 about four different directions, about the x, y, and z cartesian coordinate axes and about fourth (labeled "C") radial direction about the axial line between chuck/vise 92 and tailstock 94. Table or frame 96 supports chuck/vise 92 and tailstock 94 and includes mechanisms for moving chuck/vise 92 and tailstock 94 horizontally and laterally, i.e., in the x and y directions. Chuck/vise 92 securely clamps on one end of stock material 90 and pins the other end against the rotatable surface of tailstock 94, allowing for the rotation of stock material 90 about axis C. Milling drill 98 is positioned above frame 96, and drill 98 is adapted to move vertically, in the z direction, and bring milling drill 98 into contact with stock material 90.

CNC machine 88 receives numerical instructions which causes the mechanisms of frame 96 and drill 98 to bring stock material 90 into contact with milling drill 98, to thereby drill out the unwanted material and provide the desired implant shape. Milling drill 98 may have any one of several different types and sizes of drill bits, as described below. CNC machine 88 and chuck/vise 92 are conventionally arranged so that stock material 90 may be rotated in 90° increments, so that all four sides may be formed, namely the medial, lateral, posterior, and anterior sides of the femoral stem implant.

The machining program, which cuts the implant out of metal, depends solely on the geometry of the implant. The algorithm depends upon the 3-D geometry cross sections, of which there are 100, to guide the tool path from point to point in each section. The program uses several different tools to machine certain areas of the implant.

The program assumes the CNC machine will use 3 inch×2 inch piece of titanium stock which is typically 18 inches long. The first step is to drill an extraction hole into the implant. The extraction hole is defined by the midpoint coordinates in both the X and Y direction for section 79. The extraction hole serves not only a mechanical purpose but also as a reference point for all dimensions on the stem. The extraction hole is created by using a center drill and a boring drill. The center drill taps a lead hole into the stock which then is followed by using the boring drill which drills a hole straight through the implant to the other side. The extraction hole is machined with the stock at position 0°.

The next process uses a ¾ inch flat end mill to "profile and rough out" the stock. The program determines the minimum and maximum X, Y, and Z values for each cross section to define an outline or profile of the implant. The anterior and posterior profiles of the implant are cut at 90° and 270°. The program instructs the CNC machine to rotate the stock to either 90°, 180°, 270°, or 0° depending on which side of the stem is being surfaced.

The profiling portion of the program follows in a certain order. The medial and lateral portions of the implant are profiled first at 0° then rotated to 180°. Profiling of the neck region, which is defined by sections 80 through 100, is not performed until all of the A/P and M/L profiles of the lower sections have been cut. This keeps the stock study and the implant from torquing because a large portion of the material around the neck area has to be removed. Once the medial and lateral profiles have been cut, the machine rotates the stock at 90° at which point the ¾ inch flat end mill makes several straight passes to clear out excess stock and a final contour pass is made with the tool to define the exact shape of the implant. The contour pass follows the implant as defined by the minimum and maximum Z coordinates and X coordinates. Only a bowed stem implant will require a contour of the posterior side. Meanwhile, the anterior side is always contoured. Once this has been performed at 90°, the stock is rotated to 270°. The same process of straight line profiling and contouring is performed. The only difference between 90° and 270° is in the position of the tool where the Y coordinates are changed from positive to negative and vice versa. Now that the excess stock has been cleared to create a profile up to section 80 for both the medial/lateral and anterior/posterior sections, the machining algorithm will follow the profile of the neck region as defined by sections 80 through 100. The stock is rotated to 180° where the machine will clear out the excess stock in the neck region. Then, the stock is rotated to 0° and the excess stock is cleared out above the neck region. At this point, the profiling aspect of the machining techniques have been finished.

Once the extraction hole and profiles have been completed, the stock is rotated to 0° and surfacing of the implant begins. A ¾ inch ball end mill is used to clear excess stock from the neck and proximal anterior region. The ¾ inch ball end mill follows the contour of the neck region as defined from sections 81 to 100. The tool starts at the stock edge Y position and X position of section 100. Then the tool moves medially to the Y position of section 100, follows the contour from section 100 to section "neck lateral point", at which time the tool continues down to section 81 and then moves laterally in the Y direction. The neck lateral point is defined as the lowest X coordinate neck point (90>neck point>100) which is greater than the maximum X coordinate of section 81. The tool then traverses to section 100 again at the new coordinates. The same process takes place as the tool path is defined from section 100 down to the neck lateral point traversing over to section 81 and back to the edge of the stock. This process continues for the top half of the implant, stepping over three section points each time. The stock is then rotated to 180° where the bottom half of the implant is machined in the same fashion.

The ¾ inch ball end mill is used to cut the contour of the proximal anterior region. This area is from sections 80 to 68 with the stock at 0°. Only the anterior half of the implant is cut.

Once the profile of the neck and proximal anterior region have been cut with the ¾ inch ball end mill, a tool change is required to use the ½ inch ball end mill. The ½ inch ball end mill is the final tool used to create the finished contour of the implant. Minimum and maximum Y values, which define the profile in the medial and lateral sections, are used as stopping and starting points for the ½ inch ball end mill. The tool is lowered to the proper depth-proper depth is defined by the Z coordinate of the starting and stopping point. The tool is then traversed from the edge of the stock into the correct X and Y position at the starting depth. Then the tool follows the contour of the implant as defined by all 40 points per section of the implant. Please note that not all 40 points will be machined on one half of the implant. Typically, the starting and stopping point of the implant usually incorporate about 20 points. The tool follows the path of approximately 20 points moving laterally going from a positive to negative Y direction, then the tool moves down the implant distally to the next section and moves from the negative Y direction going toward the positive Y direction. This process starts at section 80 and traverses down toward the distal most section 1. This will define half of the finish contour of the implant using the ½ inch ball end mill. This technique is timely, cost effective, and produces less wear on the tool being used. Once sections 1 through 80 are machined, the tool is then taken to sections 81 through 100, which defines the neck area. The same technique that was used by the ¾ inch ball end mill is used by the ½ inch ball end mill to define the neck region. The entire process of machining from section 1 through 80, and then 81 through 100 is repeated when the stock is rotated to 180°. This would then conclude the finish surfacing of the implant.

At this point, the machining steps will differ from implant to implant depending upon the parameters chosen by the engineer. If a proximal pocket has been selected, the ¼ inch ball end mill is chosen. From sections 76 to 58, the ¼ inch ball end mill is used to machine a pocket which is offset 0.045 inches deep into the implant. The pocket offset is machined in the same fashion as the geometry of the stem was machined. In other words, the tool moves from the positive Y position to the negative Y position decrements down to the next section (or x value) and moves from the negative Y position to the positive Y position. This continues from section 76 through 58. Each section has an additional two sections interpolated between it and the next section. For example, the space between section 58 through 59 would be sliced into three fractional sections, thus providing a more defined pocket area. This provides a total of three times 18 sections, or 54 sections, in the pocket area. Each section has 80 points which further define the pocket area. The aforementioned process has the advantage of more particularly defining the pocket.

With the contour of the implant and the pocket finished, the machine can now use a 1 inch woodriff cutter to cut flutes on three sides of the stem. The flutes follow the 3 dimensional coordinates from sections 1 through 35 of the implant. The flutes are put on the medial, anterior, and posterior sides of the implant. Also, if a pocket was not used then macro-fit grooves may be cut into the implant using a 5/64 inch flat end mill. The 5/64 inch flat end mill follows the contour of the geometry offset 0.045 inches into the implant. Three straight lines, defining grooves, are cut on the anterior and posterior sides of the implant.

Finally, witness marks are cut on the most distal and most proximal portion of the implant using a ¼ inch ball end mill. These witness marks allow the machinist to cut off the implant at the proper position with respect to the entire piece of stock. The witness mark keeps the implant at the correct length and the neck at the correct length. The machine process has now been finished with special attention going toward the machining process of the pocket and of the surfacing of the implant from sections 1 through 80.

Manufacture of a Rasping Broach

Figure 13:
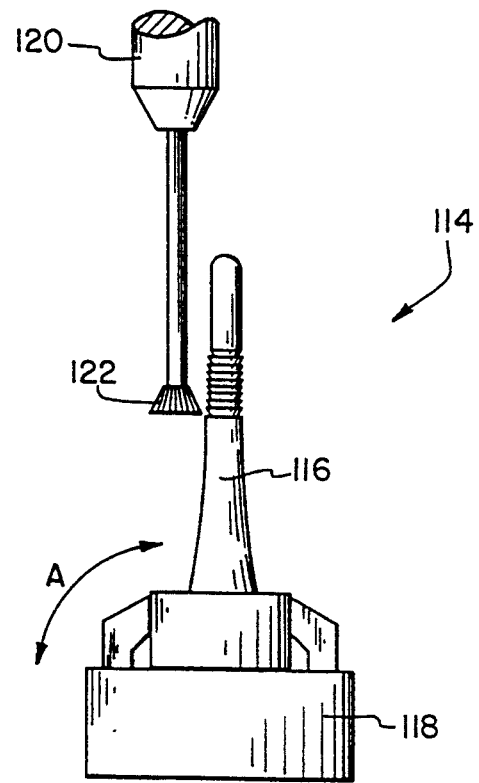
FIG. 13 is a perspective view of a five axis machine milling a piece of stock material for forming a rasping broach.

The apparatus which manufactures the femur stem rasping broach is shown in FIG. 13. CNC machine 114 is similar to CNC machine 88 of FIG. 12, and is termed a five axis machine for its ability to move stock material 116 about five different directions. CNC machine 114 may move stock material about the x, y, and z cartesian coordinate axes and the fourth radial direction shown in FIG. 12, and additionally in a fifth (labeled "A") radial direction as shown in FIG. 13. The fourth or C radial direction is about the axial line between chuck/vise 118 and the tailstock (not shown in FIG. 13). The fifth or A radial direction is about another line which is orthogonal to the axial line defining the C radial direction. In other respects, CNC machine 114 operates similarly to a four axis machine, but includes the ability to rotate horizontally disposed stock material 116 and position it vertically for further milling. As the end of stock material 116 which was abutting the tailstock no longer needs a second end, as that second end of stock material 116 is cut off so that milling drill 120 can access portions of stock material 116.

The first step in manufacturing a rasping implant is to mill a piece which is approximately the shape of the implant by the process describe above. However, the smooth surfaces of the piece produced by the milling operations are stepped in this teeth forming process by specially designed angled drill bit or cutter 122 which is generally trapezoidally shaped in cross-section. The angled drilling bit cuts into the surface of the implant and provides the stepped surface which is desired for rasping. Alternatively, a flat surface drill bit may be used as long as stock material 116 may be positioned at transverse, non-perpendicular angles, although the resulting stepped surface would have right angled teeth rather than the acute angled teeth possible with drill bit cutter 122.

Only the most proximal two thirds of stock material 116 is machined to make the rasp broach. Because the most proximal portion of the rasp is the lowest portion of stock material 116 in FIG. 13, the higher numbered sections of the rasp are actually the lower portions of stock material 116 in FIG. 13. From section 1 to 40 of the geometry, the stem is cylindrical. Above section 40, the rasp broach's geometry is determined in the same manner as the implant geometry is determined, and thus the final rasp broach includes the contour of sections 100 to 40, which are the middle and upper portions of the stem implant, along with an additional inch of the cylindrical portion. The distal cylindrical portion is utilized for guiding the rasping broach into the medullary canal, whereas the middle and proximal sections are used for the actual rasping of the femur.

To manufacture the rasp broach, stock material 116 is fixed between chuck/vise 118 and the tailstock, allowing for rotation about the C axis only. The lower and middle sections are milled in a manner similar to that described above in the manufacture of the implant, however, the neck portion of the rasp broach is not initially milled. By keeping the neck unprofiled or unfinished, the middle and lower portions of stock material 116 maintain a sturdy and rigid connection to the remainder of stock material 116. Next, the same finishing techniques are employed on the surface of the middle and lower portions as are done with the implant. Once the milling and finishing are completed, a ¼ inch ball end mill is used to cut the rasp broach away from the distal portion of stock material 116, at a position one inch below section 40. Now the rasp broach is physically freed from the distal portion of stock material 116 and the tailstock, allowing for the rotation of the rasp broach from a horizontal position (A axis position of −90°) to a vertical position (A axis position of 0°) in order to cut the teeth in the rasp broach.

FIG. 13 shows stock material 116 in the vertical position so that teeth may be cut into the exterior surface of the rasp broach. Teeth tool cutter 122 is generally trapezoidal in cross-section and operates similarly to a horizontally spinning saw blade. Multiple passes of cutter 122 are applied to the rasp broach to create a plurality of vertically disposed teeth, arranged in layers. Each pass of cutter 122 involves cutting around the perimeter of the desired z coordinate section. Each z coordinate section is defined by the closest x, y coordinates in the section. Since each of the 100 sections defining the implant and the rasp broach are not parallel to each other, a computer algorithm is used to find the closest x, y coordinates that have a z coordinate nearest to the desired section. This computer algorithm may be any of a number of well known algorithms, including but not limited to linear interpolation, least squares analysis, etc.

For example, assume the desired teeth level for the current pass is a z coordinate located at 2 inches from the extraction hole. Many sections may have x, y coordinates with z values near or at 2 inches. Therefore, for each of the points located in section near the 2 inch mark, a comparison is performed to find which forty x, y points best fit the desired teeth level. Once the forty points for that z section have been determined, cutter 122 is guided according to the determined points to cut a depression about 0.045 inches deep into the rasp broach. This process is continued from the most distal section (one inch below section 40) to the most proximal section below the neck (section 80).

Figure 14:
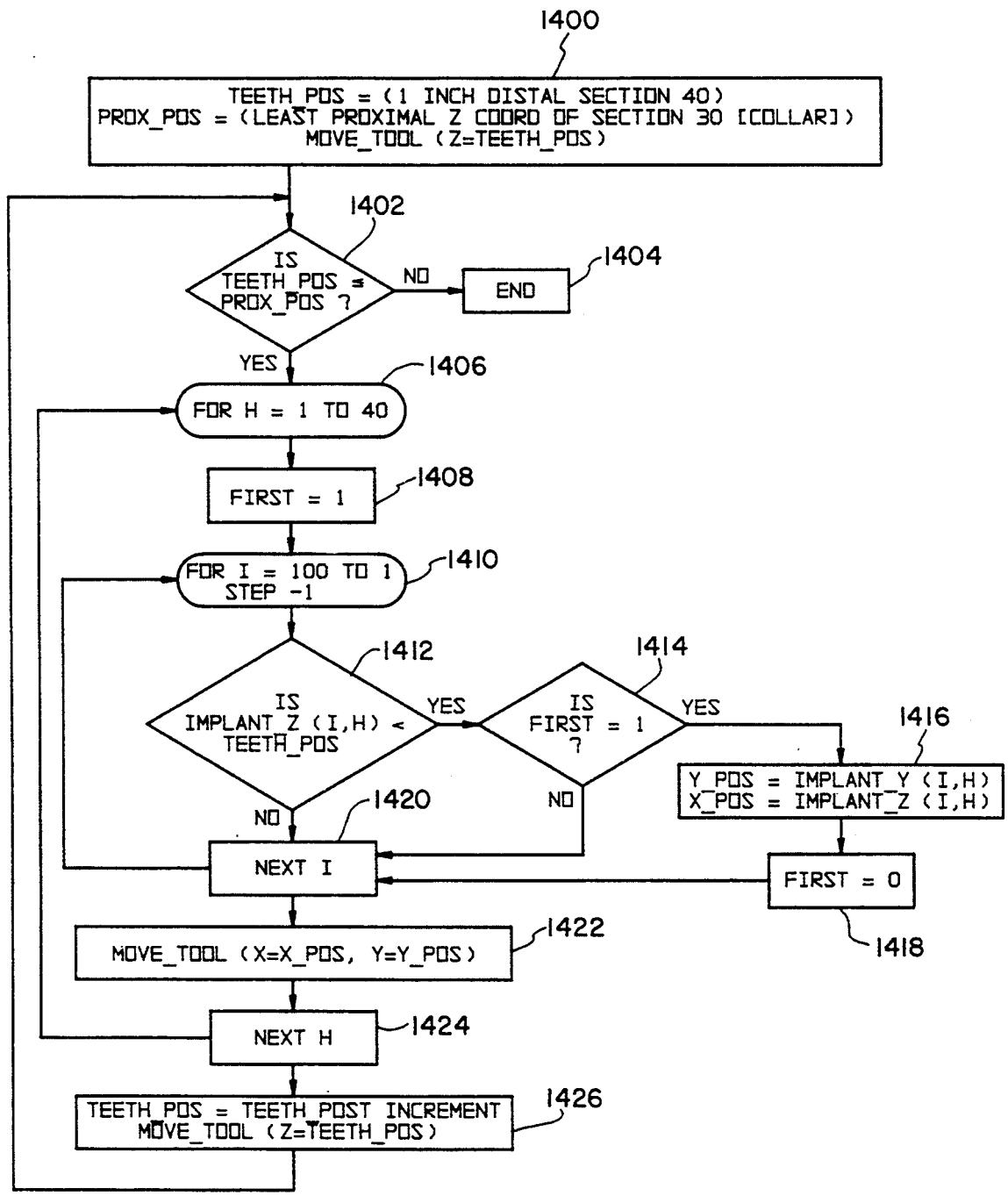
FIG. 14 is a flow chart diagram of the cutting control algorithm used for manufacturing the rasp broach.

During the first step of manufacturing the rasp broach wherein stock material 116 is generally horizontally disposed, the topology as defined by the forty cross-sections is oriented such that the x coordinates run from the distal to proximal sides of the rasp broach, the y coordinates run from the lateral to medial sides, and the z coordinates run from the posterior to anterior sides. However, once stock material 116 is rotated to its generally vertical orientation, the x coordinates now run from the posterior to anterior sides and the z coordinates now run from the distal to proximal sides. The y coordinates remain the same, because in effect the axial center of stock material 116 is switched from the x axis to the z axis. In order to generate the correct sequence of machine tool instructions from the data model based on a different orientation of axes, the algorithm shown in the flow chart of FIG. 14 is employed.

The algorithm starts with initialization step 1400 wherein the current cutting tool position the most proximal position are given their initial values and cutter 122 is moved to the first z position. Specifically, the current cutting tool position is represented by "Teeth_pos", which is set to the z coordinate which is one inch distal of section 40. The most proximal position is represented by "Prox_pos", which is set to a z coordinate which is located on the collar, section 80. Cutter 122, initially positioned at an x, y coordinate outside of the span of stock material 116, is moved to a z coordinate corresponding to the value of the variable "Teeth_pos". At this point, CNC machine 114 is ready to cut the first row of teeth and advance to the next row of teeth in the looping procedure described below.

The loop continues until the value of Teeth_pos exceeds the value of Prox_pos as tested in step 1402. If Teeth_pos exceeds Prox_pos, then the cutting is ended in step 1404 by moving cutter 122 away from stock material 116 so that chuck/vise 118 is moved about the A axis to return stock material to a horizontal orientation for finishing of the neck sections. However, if further portions of the rasp broach remain to be cut, then cutter 122 is moved around forty perimeter points which most closely match the implant topology.

This is done by FOR loop 1406 wherein the variable "h" is used to index the forty points in single increments from one to forty. After h loop step 1406, step 1408 sets the variable "First" to the value of 1. Then another FOR loop starts at 1410, which uses the variable "i" to index the 100 different levels of the implant topology by searching through the 100 sections in descending order for the best z coordinate fit. After i loop step 1410, the z coordinate value of the implant at the $i^{v\theta}$ level of the $h^{v\theta}$ radial point (which is stored at the i, h index of the two dimensional "implant_z" array) is compared to the current value of Teeth_pos. If that z coordinate value is less than Teeth_pos then the value of First is determined in step 1414. If First is equal to 1, then the variables "y_pos" and "x_pos" are set to the corresponding y and z values, respectively, in step 1416. Specifically, y_pos is set to the y coordinate value at the $i^{v\theta}$ level of the $h^{v\theta}$ radial point (which is stored at the i, h index of the two dimensional "implant_y" array) and x_pos is set to the z coordinate value at the $i^{v\theta}$ level of the $h^{v\theta}$ radial point (which is stored at the i, h index of the two dimensional "implant_z" array). Next, in step 1418 the value of First is set to 0.

If implant_z(i, h) is greater than the current value of Teeth_pos in step 1412, or if First is not equal to 1 in step 1414, or after the completion of step 1418, the i loop continues in step 1420 by returning to step 1410 and decrementing the value of i by one before iterating the loop again. After the last iteration of the i loop, cutter 122 is moved to the new x and y coordinates indicated by the variables x_pos and y_pos in step 1422.

After moving to the specified peripheral point, the determination of the next peripheral point continues by continuing the h loop in step 1424, wherein the value of h is incremented by one in step 1406 and the h loop repeated. Once all forty points have been identified and cutter 122 moved around to cut a row of teeth, cutter 122 is moved to the next level in step 1426. Specifically, the value of Teeth_pos is increased by a predetermined increment, and cutter 122 is moved to an x, y position removed from stock material 116 and to the z position indicated by the value of Teeth_pos. Then the process continues by returning to step 1402 to determine if Teeth_pos has exceeded Prox_pos, and thus teeth have been formed up to the collar.

Once the teeth have been cut, stock material 116 is rotated about the A axis to a position of −90°. With stock material 116 now in a horizontal position, the milling and finishing of the neck may commence. The same techniques used in manufacturing the implant neck portion are used to create the rasp broach neck portion. Once the neck milling and finishing are accomplished, the ¼ inch ball end mill is employed to create a witness mark at the most proximal cut off point for the neck. The resulting rasp broach has a sawtooth arrangement of edges and depressions in its middle, with the lower cylindrical portion only being an inch in length, and the upper neck portion being similarly shaped to the neck portion of the implant.

An alternative method of creating teeth in the surface of the rasp broach involves using a conventional flat mill and varying the position of the stock material about all five axes of CNC machine 114. This involves selecting the points on the sections as previously described, and further includes the generation of machine instructions which moves the stock material in such a manner so that the mill cuts teeth at the desired location. This method is much more complicated, requires much more mechanical movements, and would thus be slower than using the conventional technique of guiding the cutter around the defined perimeter. Further, the use of a straight mill creates depressions with a 90° angle, rather than the acute angle depressions created by cutter 122.

Exemplary Embodiment

In the exemplary embodiment, the computer system used includes a 486 microprocessor capable of operating at a speed of 33 mHz, made by Intel Corporation of Santa Clara, Calif., and having at least 4 megabytes of random access memory (RAM). The Windows 3.0 or later version, by Microsoft Corporation of Seattle, Wash., is employed on the computer system for its graphic user interface. Also, for visual clarity, a 1024×768 pixel monitor having 256 color scales was used. For printing, a laser printer was used, such as a Hewlett-Packard LaserJet III. The scanner used was a Truvel TZ3X x-ray image scanner, made by Truvel of Hernden, Va., a division of VIDAR Systems Corp., which is able to identify 256 grey scale values and produce a data file in the well known .TIF image storage format.

The CNC machinery used may be any suitable four axis machine for the manufacture of the implant, or any suitable five axis machine for the manufacture of the rasp broach. The CNC machinery is preferably made a Lebland Makino of Japan which utilizes a Fanuc Type Contronller and allows for the automatic instruction driven machining of stock material While this invention has been described as having a preferred design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of designing a prosthetic implant, said method utilizing first and second two dimensional x-ray radiograph images relating to the location of the implant, said method comprising the steps of:
   optically scanning and digitizing the first and second two dimensional x-ray radiograph images to create representation of the first and second two dimensional x-ray radiograph images and electronically storing said representations;
   displaying said representations of the first and second two dimensional x-ray radiograph images;
   selecting a first and second plurality of points on said first and second representations which correspond to the location for the implant;
   storing said first and second plurality of points in association with location information of said first and second plurality of points on said representations; and
   calculating a topology for a prosthetic implant using said first and second plurality of points.

2. The method of claim 1 further including the step of displaying an outline view of said calculated topology.

3. The method of claim 2 wherein said outline view corresponds to one of said first and second images.

4. The method of claim 1 wherein the first and second two dimensional x-ray radiograph images are magnified by a corresponding magnification factor, and said selecting step includes normalizing said first and second plurality of points to the corresponding magnification.

5. The method of claim 1 further comprising the step of generating a series of machine tool instructions for manufacturing a prosthetic implant according to said calculated topology.

6. The method of claim 5 further comprising the step of manufacturing a prosthetic implant generally having an outer surface corresponding to said calculated topology.

7. The method of claim 1 wherein said implant is to be attached within a bone canal having generally parallel sides, and said selecting step includes selecting an axial center of said canal on said first representation and adjusting the position of two lines which are parallel and equidistant to said axial center on said first representation.

8. The method of claim 7 wherein said selecting step further includes selecting additional contour points extending from said straight sides of said canal.

9. The method of claim 7 wherein said selecting step includes selecting an axial center of said canal on said second representation and automatically creating and displaying two lines which are parallel and equidistant to said axial center on said second representation.

10. The method of claim 1 further comprising the step of displaying a template of said calculated topology with one of said first and second representations.

11. The method of claim 1 further comprising the step of altering at least one of said points of said first and second plurality of points then recalculating a new implant topology using said first and second plurality of points.

12. An apparatus for designing a prosthetic implant, said apparatus utilizing first and second two dimensional x-ray radiograph images relating to the location of the implant, said apparatus comprising:
   means for optically scanning and digitizing the first and second two dimensional x-ray radiograph images to create representations of the first and second two dimensional x-ray radiograph images and electronically storing said representations;
   means for displaying said representations;
   means for selecting a first and a second plurality of points on said first and second representations which correspond to the location for the implant;
   means for storing said first and second plurality of points in association with location information of said first and second plurality of points on said representations; and
   means for calculating a topology for a prosthetic implant using said first and second plurality of points.

13. The apparatus of claim 12 wherein said displaying means includes means for displaying a sectional view of said calculated topology.

14. The apparatus of claim 13 wherein said sectional view corresponds to one of said first and second two dimensional x-ray radiograph images.

15. The apparatus of claim 12 wherein the first and second two dimensional x-ray radiograph images are magnified by a corresponding magnification factor, and said selecting means includes means for normalizing said first and second plurality of points to the corresponding magnification.

16. The apparatus of claim 12 further comprising means for generating a series of machine tool instructions for manufacturing a prosthetic implant according to said calculated topology.

17. The apparatus of claim 16 further comprising means for manufacturing a prosthetic implant generally having an outer surface corresponding to said calculated topology.

18. The apparatus of claim 12 wherein said implant is to be attached within a bone canal having generally parallel sides, and said selecting means includes means for selecting an axial center of said canal on said first representation and means for adjusting the position of two lines which are parallel and equidistant to said axial center on said first representation.

19. The apparatus of claim 18 wherein said selecting means further includes means for selecting additional contour points extending from said cylindrical canal.

20. The apparatus of claim 18 wherein said selecting means includes means for selecting an axial center of said canal on said second representation and means for automatically creating and displaying two lines which are parallel and equidistant to said axial center on said second representation.

21. The apparatus of claim 12 wherein said displaying means includes means for presenting a template of said calculated topology with one of said first and second representations.

22. The apparatus of claim 12 further comprising means for altering at least one of said points of said first and second plurality of points then recalculating a new implant topology using said first and second plurality of points.

23. A method of designing a prosthetic implant, said method utilizing first and second two dimensional x-ray radiograph images relating to the location of the implant, said method comprising the steps of:
   optically scanning and digitizing the first and second two dimensional x-ray radiograph images to create representations of the first and second two dimensional x-ray radiograph images and electronically storing said representations;
   displaying said representations of the first and second two dimensional x-ray radiograph images;
   selecting a first and a second plurality of points on said first and second representations which correspond to the location for the implant;
   storing said first and second plurality of points in association with location information of said first and second plurality of points on said representations;
   calculating a topology for a prosthetic implant using said first and second plurality of points; and
   generating a series of machine tool instructions for manufacturing a prosthetic implant according to said calculated topology.

24. A method of designing a prosthetic implant, said method utilizing first and second two dimensional x-ray radiograph images relating to the location of the implant, said method comprising the steps of:
   optically scanning and digitizing the first and second two dimensional x-ray radiograph images to create representations of the first and second two dimensional x-ray radiograph images and electronically storing said representations;
   displaying said representations of the first and second two dimensional x-ray radiograph images;
   selecting a first and a second plurality of points on said first and second representations which correspond to the location for the implant;
   storing said first and second plurality of points in association with location information of said first and second plurality of points on said representations;
   calculating a topology for a prosthetic implant using said first and second plurality of points; and
   manufacturing a prosthetic implant generally having an outer surface corresponding to said calculated topology.

* * * * *